United States Patent
Morre et al.

(10) Patent No.: US 9,891,222 B2
(45) Date of Patent: Feb. 13, 2018

(54) METHODS AND COMPOSITIONS FOR IDENTIFICATION AND QUANTIFICATION OF ENOX2 TRANSCRIPT VARIANTS AS INDICATIONS OF CANCER PRESENCE IN BLOOD SERUM AND OTHER BODY FLUIDS BASED ON GOLD OR SILVER NANOPARTICLE FORMATION

(71) Applicants: Mor-Nuco Enterprises, Inc., West Lafayette, IN (US); Nicholas J. Miner, Lafayette, IN (US)

(72) Inventors: D. James Morre, West Lafayette, IN (US); John Orczyk, West Lafayette, IN (US)

(73) Assignee: Mor-Nuco Enterprises, Inc., West Lafayette, IN (US)

( * ) Notice: Subject to any disclaimer, the term of this patent is extended or adjusted under 35 U.S.C. 154(b) by 0 days.

(21) Appl. No.: 15/587,072

(22) Filed: May 4, 2017

(65) Prior Publication Data
US 2017/0322214 A1  Nov. 9, 2017

Related U.S. Application Data

(60) Provisional application No. 62/332,353, filed on May 5, 2016.

(51) Int. Cl.
| | |
|---|---|
| *G01N 33/574* | (2006.01) |
| *A61K 39/395* | (2006.01) |
| *C07K 16/40* | (2006.01) |
| *G01N 27/447* | (2006.01) |

(52) U.S. Cl.
CPC ......... *G01N 33/574* (2013.01); *A61K 39/395* (2013.01); *C07K 16/40* (2013.01); *G01N 27/447* (2013.01)

(58) Field of Classification Search
None
See application file for complete search history.

(56) References Cited

U.S. PATENT DOCUMENTS

| | | | |
|---|---|---|---|
| 7,053,188 B2 * | 5/2006 | Morre | G01N 33/57492 530/388.1 |
| 9,283,257 B2 | 3/2016 | Morre | |
| 9,459,256 B2 | 10/2016 | Morre | |
| 9,612,243 B1 | 4/2017 | Morre et al. | |
| 2003/0207340 A1 | 11/2003 | Morre et al. | |
| 2009/0042209 A1 | 2/2009 | Hostetler | |
| 2012/0034626 A1 | 2/2012 | Morre et al. | |
| 2014/0212896 A1 | 7/2014 | Morre et al. | |

FOREIGN PATENT DOCUMENTS

| | | |
|---|---|---|
| WO | 2011109663 A1 | 9/2011 |
| WO | 2013052926 A2 | 4/2013 |

OTHER PUBLICATIONS

Xiao et al. (Anal. Chem. 2008 vol. 80, pp. 2799-2804).*
Bird, et al. "Single-chain antigen-binding proteins." Science, Oct. 21, 1988, vol. 242, No. 4877, pp. 423-426.
Braman, et al., "Site-Directed Mutagenesis Using Double-Stranded Plasmid DNA Templates," Chapter 3 of Methods in Molecular Biology, vol. 57, In Vitro Mutagenesis Protocols, 1996, pp. 31-44.
Bruno, et al., "Stimulation of NADH oxidase activity from rat liver plasma membranes by growth factors and hormones is decreased or absent with hepatoma plasma membranes" Biochemical Journal, Jun. 15, 1992, vol. 284, No. 3, pp. 625-628.
Cho, et al., "Monoclonal antibody to a cancer-specific and drug-responsive hydroquinone (NADH) oxidase from the sera of cancer patients," Feb. 27, 2002, Cancer Immunol. Immunother. 51, pp. 121-129.
Chomczynski, et al. "Single-step method of RNA isolation by acid guanidinium thiocyanate-phenol-chloroform extraction," 1987, Analytical Biochemistry, vol. 162, pp. 156-159.
Chueh, et al., "Molecular Cloning and Characterization of a Tumor-Associated, Growth-Related, and Time-Keeping Hydroquinone (NADH) Oxidase (tNOX) of the HeLa Cell Surface," Jan. 11, 2002, Biochemistry, vol. 44, pp. 3732-3741.
Daugherty, et al., "Polymerase chain reaction facilitates the cloning, CDRgrafting, and rapid expression of a murine monoclonal antibody directed against the CD18 component of leukocyte integrins," Mar. 25, 1991, Nucleic Acids Research, vol. 19, No. 9, pp. 2471-2476.
Davies, et al., "Spotlight on tNOX: A tumor-selective target for cancer therapies," May 2006, Drug News Perspect vol. 19(4), pp. 223-225.
Davis, et al. "Single Chain Antibody (SCA) Encoding Genes: One-Step Construction and Expression in Eukaryotic Cells," Feb. 1991, Bio/Technology, vol. 9, pp. 165-169.
Del Castillo-Olivares, et al., "A Drug-Responsive and Protease-Resistant Peripheral NADH Oxidase Complex from the Surface of HeLa S Cells," Oct. 1, 1998, Archives of Biochemistry and Biophysics, vol. 385, pp. 125-140.

(Continued)

Primary Examiner — Changhwa J Cheu
(74) Attorney, Agent, or Firm — Edwin S. Flores; Chalker Flores, LLP (57) ABSTRACT

The present invention includes a semi-quantitative method for the detection of ENOX2 transcript variants from one or more anti-ENOX2 antibody-binding spots on a blot comprising the steps of: electrophoretically separating proteins from a concentrated blood, serum, or plasma sample from the subject; transferring the electrophoretically separated proteins to a substrate; separating the one or more ENOX2 transcript variants from the one or more anti-ENOX2 antibody-binding spots; and measuring an ENOX2-catalyzed conversion of an ionic silver or gold to a colloidal silver or gold detected by light scattering from the one or more anti-ENOX2 antibody binding spots on the substrate, wherein each of the one or more spots is indicative of the ENOX2 transcript variant. Also provided is the basis for a point of care test to detect ENOX2 transcript variants based on use of colloidal gold or silver complexes with ENOX2 as a rapid simple test for cancer presence.

20 Claims, 4 Drawing Sheets

(56) References Cited

OTHER PUBLICATIONS

Extended European Search Report of 16180364.8 dated Nov. 11, 2016, 12 pp.
GenBank Accession No. AF207881, 3 pp, 2002.
Glockshuber, et al. "A comparison of strategies to stabilize immunoglobulin Fv fragments," 1990, Biochemistry, vol. 29, pp. 1362-1367.
Goncalves, et al., "Clinical Application of Proteomics in Breast Cancer: State of the Art and Perspectives," Medical Principles and Practice, vol. 20, No. 1, 2011, pp. 4-18.
Gough, NM "Rapid and quantitative preparation of cytoplasmic RNA from small numbers of cells," 1988, Analytical Biochemistry, vol. 173, pp. 93-95.
Hoopes, et al., "Staining Electrophoretic Gels for Laccase and Peroxidase Activity Using 1,8-Diaminonaphthalene," Analyt. Biochem., 293 (1), May 1, 2001, pp. 96-101.
Hostetler, et al. "Cancer Site-Specific Isoforms of ENOX2 (tNOX), A Cancer-Specific Cell Surface Oxidase," Sep. 2008, clin. Proteom (2009), vol. 5, pp. 46-51.
Howlander, et al. SEER Cancer Statistics Review,1975-2012, National Cancer Institute, Bethesda, MD.
Huston, et al. "Protein Engineering of Antibody Binding Sites: Recovery of Specific Activity in an Anti-Digoxin Single-Chain Fv Analogue Produced in *Escherichia coli*," Aug. 1988, Proc. Natl. Acad. Sci USA, vol. 85, pp. 5879-5883.
International Search Report and Written Opinion of Korean Intellectual Property Office for PCT/US2012/059141 dated Mar. 25, 2013, 14 pp.
Jiang, Z., et al., "Molecular Cloning and Characterization of a Candidate Human Growth-Related and Time-Keeping Constitutive Cell Surface Hydroquinone (NADH) Oxidase," Biochemistry, vol. 47, No. 52, Sep. 2008, pp. 14028-14038.
Jones, et al. "Rapid PCR-Cloning of Full-Length Mouse Immunoglobulin Variable Regions," Jan. 1991, Bio/Technology, vol. 9, pp. 88-89.
Lee et al., "Effect of BRCA1/2 mutation on short-term and long-term breast cancer survival: a systematic review and meta-analysis." Breast Cancer Research and Treatment, Jul. 2010, vol. 122, Issue 1, pp. 11-25.
Morre, et al. (1988) "Inhibition of Plasma membrane redox activities and elongation of growth of soybean," Phsiologia Plantarum, vol. 72, 1988, pp. 236-240.
Morre, et al., "The antitumor sulfonylurea N-(4-methylphenylsulfonyl)-N'-(4-chlorophenylureal) urea (LY181984) inhibits NADH oxidase activity of HeLa plasma membranes." Biochim. Biophys. Acta., 1995, vol. 1240, pp. 11-17.
Morre, et al. (1995), "Capsaicin inhibits preferentially the NADH oxidase and growth of transformed cells in culture" 1995. Proc. Natl. Acad. Sci. 92: 1831-1835.
Morre, et al., "NADH Oxidase Activity from Sera Altered by Capsaicin Is Widely Distributed among Cancer Patients" 1997. Arch. Biochem. Biophys. 342: 224-230.
Morre, et al. "A circulating form of NADH oxidase activity responsive to the antitumor sulfonylurea N-(4-methylphenylsulfonyl)-N'-(4-chlorophenyl)urea (LY181984) specific to sera from cancer patients" 1997. J. Bioenerg. Biomemb. 29: 281-289.
Morre, D.J., "NADH Oxidase: A Multifunctional Ecto-proteins of the Eukaryotic Cell Surface," In: Asard, H., Bérczi, A. and Caubergs, R., Eds., Plasma Membrane Redox Systems and Their Role in Biological Stress and Disease, Kluwer Academic Publishers, Dordrecht, Dec. 31, 1998, pp. 121-156.
Morre, D.J., et al., "Use of dipyridyl-dithio substrates to measure directly the protein disulfide-thiol interchange activity of the auxin stimulated NADH: Protein disulfide reductase (NADH oxidase) of soybean plasma membranes," Molecular and Cellular Biochemistry, vol. 200, Dec. 15, 1998, pp. 7-13.
Morre, D.J., et al., "Glaucarubolone and Simalikalactone D, Respectively, Preferentially Inhibit Auxin-Induced and Constitutie Components of Plant Cell Enlargement and the Plasma Membrane NADH Oxidase," Int. J. Plant Sci., 1999, 160(2), pp. 291-297.
Morre et al. "Surface NADH oxidase of HeLa cells lacks intrinsic membrane binding motifs," Jul. 17, 2001, Arch. Biochem. Biophys. 392: pp. 251-256.
Morre, et al., "Cell surface NADH oxidases (ECTO-NOX proteins) with roles in cancer, cellular time-keeping, growth, aging and neurodegenerative disease" Aug. 2003, Free Radical Res. 37: 795-805.
Morre, et al., "Cancer Type-Specific tNOX Isoform: A Putative Family of Redox Protein Splice Variants with Cancer Diagnostics and Prognostic Potential" Biofactors, 2009, vol. 34, No. 3, pp. 201-207.
Morre, et al., "Early Detection: An Opportunity for Cancer Prevention Through Early Intervention" Cancer Prevention—from Mechanisms to Translational Benefits, Apr. 20, 2012, pp. 389-402.
Morre, et al., "The Auxin-Stimulated ENOX and Auxin Stimulation of Plant Growth," Chapter 10 of Ecto-Nox Proteins: Growth, Cancer; Aging, Springer Science+Business Media New York 2013, pp. 313-342.
Morre, et al., "Cancer Diagnostic Applications of ENOX2 Proteins," Chapter 12 of Ecto-Nox Proteins: Growth, Cancer; Aging, Springer Science+Business Media New York 2013, pp. 419-434.
Morre, et al., "ENOX2-based early detection (ONCOblot) of asbestos-induced malignant mesothelioma 4-10 years in advance of clinical symptoms," Clin. Proteomics, 13:2, Jan. 22, 2016; 8 pp.
Smith, PK, et al., "Measurement of protein using bicinchoninic acid," Anal. Biochem., May 15, 1987, vol. 163:1: 279.
Sock, J., et al., "Activity Staining of Blotted Enzymes by Reaction Coupling with Transfer Membrane-Immobilized Auxiliary Enzymes," Analyt. Biochem., 171 (2), Nov. 16, 1987, pp. 310-319.
Tang, et al. "Alternative splicing as the basis for specific localization of tNOX, a unique hydroquinone (NADH) oxidase, to the cancer cell surface," Biochemistry, Aug. 2007, vol. 46, pp. 12337-12346.
Tang, et al., "Molecular Cloning and characterization of human age-related NADH oxidase (arNOX) proteins as members of the TM9 suprefamily of transmembrane proteins," Advances in Biological Chemistry, Apr. 2013, vol. 3, pp. 187-197.
Wang. et al., "NADH oxidase activity (NOX) and enlargement of HeLa cells oscillate with two different temperature-compensated period lengths of 22 and 24 minutes corresponding to different NOX forms," Apr. 19, 2001, Biochem Biophys. Acta, vol. 1539, pp. 192-204.
Weinberg, Robert, "Multi-Step Tumorigensis," Chapter 11, The Biology of Cancer, Garland Science, 2007, pp. 399-462.
Wu, et al., "Next-Generation Sequencing of MicroRNAs for Breast Cancer Detection." Journal of Biomedicine and Biotechnology, Mar. 24, 2011, vol. 2011, pp. 597-145.
Hanau, C., et al., "Cancer Prevention Trial of a Synergistic Mixture of Green Tea Concentrate Plus Capsicum (CAPSOL-T) in a random population of subjects ages 40-84," Clinical Proteomics, Jan. 6, 2014, vol. 11, No. 2, Internal pp. 1-11.
International Search Report and Written Opinion of Korean Intellectual Property Office for PCT/US2017/031104 dated Aug. 8, 2017, 11 pp.

* cited by examiner

A.

```
  1  MQRDFRWLNV  YEIGYAADNS  RTLNVDSTAN  TLPNSDPTAN  ATANNNRLGMA
 51  PLGIAGQPIL  PDFDPALGNM  TGIPPITPNM  PGLGIVPPPI  PPDMPVVKEI
101  IHCKSCTLFP  PNPMLPPPAI  RERPPGCKTV  PVGGLPERGY  EQIIVEVFEQ
151  CGRILAIRES  KKNFCRIRFA  EEYPVDKALY  LSGYRIRLSS  STDKKDTGRL
201  HVDFAQARDD  LYEWECKQRM  LAREERRRRK  MEESRLRPPS  PPPVVRYSDR
251  ECSIVAEKLK  DDSKFSEAVQ  TLLTRIERGE  VNRRSANNFY  SMIQSANDRV
301  RRLVNEKAAE  EKDMEEAREK  FKQALMGILI  QFEQIVAVYH  SASKQKAWDH
351  FTKAQRKNIS  VWCKQAEEIR  NIHNDELMGI  RREEEMEMSD  DEIEEMTETK
401  ETEESALVSQ  AEALKEDNDS  LRKQLDAYRN  EVELLKQEQS  KVHREDDPNK
451  EQQLKLLQQA  LQGMQQHLLK  VQEEYKKKEA  RLEKIKDDKL  QVERMLENLK
501  EKESCASRLC  ASKQESEYPL  EKTNNBSPIK  SEREALLVGI  ISTFLRVHPF
551  GASIEYICSY  LHRLDNKICT  SDVECLMGRL  QHTFKQEMTG  VGASLEKRKK
601  FCGFEGLKLY
```

[327]MGILIQFEQIVAVYHSASKQKAWDHFTKAQRKNISVWCKQAEEIRNIHNDELMGIRREEEMEMSDDEIEEMTETKETEESALVSQ[410]

[327]MGILIQFQQIVAVYHSASKQKANHFTKAQRKNISVWCKQAQQIRNIHNNQLMGIRRQQQMQMSNNQIQQMTQTKQTQQSALVSQ[410]

| Amino acid sequence of ENOX2 peptide antigen (SEQ ID NO. 2) |
|---|
| 359-SVWCKQAEEIRNIHNDE-376 |

Figure 4

SEQUENCE LISTING

```
<160> NUMBER OF SEQ ID NOS: 4

<210> SEQ ID NO 1
<211> LENGTH: 610
<212> TYPE: PRT
<213> ORGANISM: Artificial Sequence
<220> FEATURE:
<223> OTHER INFORMATION: Synthetic peptide

<400> SEQUENCE: 1

Met Gln Arg Asp Phe Arg Trp Leu Trp Val Tyr Glu Ile Gly Tyr Ala
1               5                   10                  15

Ala Asp Asn Ser Arg Thr Leu Asn Val Asp Ser Thr Ala Met Thr Leu
            20                  25                  30

Pro Met Ser Asp Pro Thr Ala Trp Ala Thr Ala Met Asn Asn Leu Gly
        35                  40                  45

Met Ala Pro Leu Gly Ile Ala Gly Gln Pro Ile Leu Pro Asp Phe Asp
    50                  55                  60

Pro Ala Leu Gly Met Met Thr Gly Ile Pro Pro Ile Thr Pro Met Met
65                  70                  75                  80
```

```
Pro Gly Leu Gly Ile Val Pro Pro Ile Pro Pro Asp Met Pro Val
                85                  90                  95
Val Lys Glu Ile Ile His Cys Lys Ser Cys Thr Leu Phe Pro Pro Asn
            100                 105                 110
Pro Asn Leu Pro Pro Ala Thr Arg Glu Arg Pro Pro Gly Cys Lys
            115                 120                 125
Thr Val Phe Val Gly Gly Leu Pro Glu Asn Gly Thr Glu Gln Ile Ile
            130                 135                 140
Val Glu Val Phe Glu Gln Cys Gly Glu Ile Ile Ala Ile Arg Lys Ser
145                 150                 155                 160
Lys Lys Asn Phe Cys His Ile Arg Phe Ala Glu Glu Tyr Met Val Asp
                165                 170                 175
Lys Ala Leu Tyr Leu Ser Gly Tyr Arg Ile Arg Leu Gly Ser Ser Thr
            180                 185                 190
Asp Lys Lys Asp Thr Gly Arg Leu His Val Asp Phe Ala Gln Ala Arg
            195                 200                 205
Asp Asp Leu Tyr Glu Trp Glu Cys Lys Gln Arg Met Leu Ala Arg Glu
            210                 215                 220
Glu Arg His Arg Arg Met Glu Glu Glu Arg Leu Arg Pro Pro Ser
225                 230                 235                 240
Pro Pro Pro Val Val His Tyr Ser Asp His Glu Cys Ser Ile Val Ala
                245                 250                 255
Glu Lys Leu Lys Asp Asp Ser Lys Phe Ser Glu Ala Val Gln Thr Leu
            260                 265                 270
Leu Thr Trp Ile Glu Arg Gly Glu Val Asn Arg Arg Ser Ala Asn Asn
            275                 280                 285
Phe Tyr Ser Met Ile Gln Ser Ala Asn Ser His Val Arg Arg Leu Val
            290                 295                 300
Asn Glu Lys Ala Ala His Glu Lys Asp Met Glu Glu Ala Lys Glu Lys
305                 310                 315                 320
Phe Lys Gln Ala Leu Met Gly Ile Leu Ile Gln Phe Glu Gln Ile Val
            325                 330                 335
Ala Val Tyr His Ser Ala Ser Lys Gln Lys Ala Trp Asp His Phe Thr
            340                 345                 350
Lys Ala Gln Arg Lys Asn Ile Ser Val Trp Cys Lys Gln Ala Glu Glu
            355                 360                 365
Ile Arg Asn Ile His Asn Asp Glu Leu Met Gly Ile Arg Arg Glu Glu
            370                 375                 380
Glu Met Glu Met Ser Asp Glu Ile Glu Glu Met Thr Glu Thr Lys
385                 390                 395                 400
Glu Thr Glu Glu Ser Ala Leu Val Ser Gln Ala Glu Ala Leu Lys Glu
            405                 410                 415
Glu Asn Asp Ser Leu Arg Trp Gln Leu Asp Ala Tyr Arg Asn Glu Val
            420                 425                 430
Glu Leu Leu Lys Gln Glu Gln Gly Lys Val His Arg Glu Asp Pro
            435                 440                 445
Asn Lys Glu Gln Gln Leu Lys Leu Leu Gln Gln Ala Leu Gln Gly Met
            450                 455                 460
Gln Gln His Leu Leu Lys Val Gln Glu Tyr Lys Lys Lys Glu Ala
465                 470                 475                 480
Glu Leu Glu Lys Leu Lys Asp Asp Lys Leu Gln Val Glu Lys Met Leu
            485                 490                 495
```

```
Glu Asn Leu Lys Glu Lys Glu Ser Cys Ala Ser Arg Leu Cys Ala Ser
                500                 505                 510

Asn Gln Asp Ser Glu Tyr Pro Leu Glu Lys Thr Met Asn Ser Ser Pro
            515                 520                 525

Ile Lys Ser Glu Arg Glu Ala Leu Leu Val Gly Ile Ile Ser Thr Phe
        530                 535                 540

Leu His Val His Pro Phe Gly Ala Ser Ile Glu Tyr Ile Cys Ser Tyr
545                 550                 555                 560

Leu His Arg Leu Asp Asn Lys Ile Cys Thr Ser Asp Val Glu Cys Leu
                565                 570                 575

Met Gly Arg Leu Gln His Thr Phe Lys Gln Glu Met Thr Gly Val Gly
            580                 585                 590

Ala Ser Leu Glu Lys Arg Trp Lys Phe Cys Gly Phe Glu Gly Leu Lys
        595                 600                 605

Leu Thr
    610

<210> SEQ ID NO 2
<211> LENGTH: 85
<212> TYPE: PRT
<213> ORGANISM: Artificial Sequence
<220> FEATURE:
<223> OTHER INFORMATION: Synthetic peptide

<400> SEQUENCE: 2

Met Gly Ile Leu Ile Gln Phe Glu Gln Ile Val Ala Val Tyr His Ser
1               5                   10                  15

Ala Ser Lys Gln Lys Ala Trp Asp His Phe Thr Lys Ala Gln Arg Lys
            20                  25                  30

Asn Ile Ser Val Trp Cys Lys Gln Ala Glu Glu Ile Arg Asn Ile His
        35                  40                  45

Asn Asp Glu Leu Met Gly Ile Arg Arg Glu Glu Glu Met Glu Met Ser
    50                  55                  60

Asp Asp Glu Ile Glu Glu Met Thr Glu Thr Lys Glu Thr Glu Glu Ser
65                  70                  75                  80

Ala Leu Val Ser Gln
            85

<210> SEQ ID NO 3
<211> LENGTH: 85
<212> TYPE: PRT
<213> ORGANISM: Artificial Sequence
<220> FEATURE:
<223> OTHER INFORMATION: Synthetic peptide

<400> SEQUENCE: 3

Met Gly Ile Leu Ile Gln Phe Gln Gln Ile Val Ala Val Tyr His Ser
1               5                   10                  15

Ala Ser Lys Gln Lys Ala Trp Asn His Phe Thr Lys Ala Gln Arg Lys
            20                  25                  30

Asn Ile Ser Val Trp Cys Lys Gln Ala Gln Gln Ile Arg Asn Ile His
        35                  40                  45

Asn Asn Gln Leu Met Gly Ile Arg Arg Gln Gln Met Gln Met Ser
    50                  55                  60

Asn Asn Gln Ile Gln Gln Met Thr Gln Thr Lys Gln Thr Gln Gln Ser
65                  70                  75                  80

Ala Leu Val Ser Gln
            85
```

```
<210> SEQ ID NO 4
<211> LENGTH: 17
<212> TYPE: PRT
<213> ORGANISM: Artificial Sequence
<220> FEATURE:
<223> OTHER INFORMATION: Synthetic peptide

<400> SEQUENCE: 4

Ser Val Trp Cys Lys Gln Ala Glu Glu Ile Arg Asn Ile His Asn Asp
1               5                   10                  15
Glu
```

METHODS AND COMPOSITIONS FOR IDENTIFICATION AND QUANTIFICATION OF ENOX2 TRANSCRIPT VARIANTS AS INDICATIONS OF CANCER PRESENCE IN BLOOD SERUM AND OTHER BODY FLUIDS BASED ON GOLD OR SILVER NANOPARTICLE FORMATION

CROSS-REFERENCE TO RELATED APPLICATIONS

This application claims priority to U.S. Provisional Application Ser. No. 62/332,353 filed May 5, 2017, the entire contents of which are incorporated herein by reference.

FIELD OF THE INVENTION

The present invention relates generally to a novel method for early cancer detection based on silver or gold nanoparticle formation by ENOX2 molecules present in blood serum and other body fluids.

BACKGROUND OF THE INVENTION

Ecto-Nicotinamide Adenine Dinucleotide Oxidase Disulfide-Thiol Exchanger (ENOX) proteins are a family of cell surface enzymes that exhibit both a hydroquinone (NADPH) oxidase and a protein disulfide-thiol interchange activity (Morré and Morré, 2013, Ecto-Nox Proteins. New York: Springer). These two enzymatic activities are essential for the expansion phase of cell proliferation (Morré and Morré, 2003. Free Radical Res. 37: 795-808). Unlike other human ENOX family members that are regulated by growth factors, the enzymatic activity of ENOX2 (also called ECTO-NOX2 or tNOX) is constitutively active and unresponsive to hormone signaling. Importantly, ENOX2 is completely absent from normal cells, except during the early stages of embryogenesis where ENOX2 activity may contribute to rapid cell proliferation. However, ENOX2 expression is also invariably induced during the benign to malignant transition of cancer cells. Thus, ENOX2 represents an oncofetal antigen and its expression universally coincides with oncogenic progression leading to malignancy.

ENOX2 is a terminal hydroquinone oxidase of the plasma membrane electron transport chain that is universally produced by malignancies, and the activity of ENOX2 significantly contributes to the unregulated growth that typifies cancer. Inhibitors of ENOX2 induce apoptosis in cancer cells, but not in non-cancer cells, an indication that the enzymatic activity of ENOX2 strongly contributes to the unregulated expansion and survival of cancer cells.

Tissue-specific ENOX2 isoforms are produced as a result of differential mRNA splicing (Tang et. al., 2007. Oncol. Res. 16: 557-567; Tang et. al., 2007. Biochemistry 46: 12337-12346). Therefore, different ENOX2 isoforms are expressed by cancers of different cellular or tissue origin. However, each ENOX2 isoform contains an identical core domain that is essential for ENOX2 enzymatic activity, allowing for immunodetection of the core region of all ENOX2 isoforms by using a single recombinant antibody (Hostetler et. al., 2009. Clin. Proteomics 5: 46-51).

ENOX2 protein expression is detected exclusively in the sera of cancer patients, but is completely absent from the sera of non-cancer patients. Therefore, unlike most cancer markers, ENOX2 is not simply produced at higher levels by cancer cells relative to non-cancer cells. ENOX2 expression has been detected from every type of malignancy tested to date, including: bladder, breast, cervical, colorectal, endometrial, esophageal, gastric, liver, kidney, lung (small and non-small cell), ovarian, pancreatic, prostate, follicular thyroid, papillary thyroid, and endometrial (uterine) cancers (Morré and Morré, 2013, Ecto-Nox Proteins. New York: Springer; Hostetler et. al., 2009. Clin. Proteomics 5: 46-51). The wide diversity of cancer types that have been found to produce ENOX2 indicates that ENOX2 expression is a conserved feature of most, and potentially all, malignancies. Thus, the cell-surface ENOX2 enzyme emerges as a universal cancer marker.

SUMMARY OF INVENTION

Based on unique secondary sequence characteristics of ENOX2 proteins resulting in quantifiable reduced gold or silver nanoparticle formation a new assay was developed and demonstrated herein. For example, it is shown herein that all 36 potential transcript variants represented in the ONCOblot® Tissue of Origin Test Data Base producing visible immunoreactive spots yielded values following reaction with tetrasilver tetroxide ≥7% background (average 12%) consistent with a structure containing the common exon 5 that defines ENOX2 proteins structurally and functionally and includes the ENOX2 specific antibody and drug-combining site E145EMTE of SEQ ID NO:1. Thus, all 36 potential transcript variants represented in the ONCOblot® Tissue of Origin Test Data Base qualify as ENOX2 transcript variants. Additionally, the property of ENOX2 proteins to form characteristic reduced gold or silver nanoparticles is described as the basis for a novel point-of-care strip test to indicate cancer presence in blood serum amenable to use by physicians for routine cancer screening.

One embodiment of the present invention includes a semi-quantitative method for the detection of ENOX2 transcript variants from one or more anti-ENOX2 antibody-binding spots comprising the steps of: electrophoretically separating proteins from a concentrated blood, serum, or plasma sample from the subject; transferring the electrophoretically separated proteins to a substrate; separating the one or more ENOX2 transcript variants from the one or more anti-ENOX2 antibody-binding spots; and measuring an ENOX2-catalyzed conversion of an ionic gold or silver to colloidal silver or gold detected by light scattering from the one or more anti-ENOX2 antibody binding spots on the substrate, wherein each of the one or more spots is indicative of an ENOX2 transcript variant. In one aspect, the quantitation is achieved by removing ENOX2 antibody reactive spots from the blot with a cork borer and quantitating the amount of ENOX2 using elution and reaction with ionic silver or gold to form silver or gold nanoparticles and their quantitation measured by light scattering when compared to a background sample. In another aspect, a signal above a background confirms the present of the ENOX2 transcript variant. In another aspect, the method further comprises the step of measuring the ENOX2-catalyzed conversion of ionic silver to colloidal silver or gold is defined further as comprising the steps of: obtaining a core from the one or more anti-ENOX2 antibody-binding spots suspected of comprising at least one ENOX2 transcript variant separated by molecular weight and isoelectric point; incubating the core with silver oxide in solution to form colloidal silver or gold; and developing the colloidal silver; and measuring the amount and/or presence of colloidal silver at 350-650 nm by comparing the light from the core with light from a background core that did not contain an ENOX2 transcript variant. In another aspect, the light scattering is a doublet at 469.3 and 469.7 nm. In another aspect, blood cell, lymphomas, leukemias, multiple myelomas and myelomas, breast, cervical, colorectal, esophageal, gastric, hepatocellular, small cell lung, non-small cell lung, melanoma, mesothelioma, ovarian, pancreatic, prostate, renal cell (kidney), sarcoma, squamous cell, testicular germ cell, thyroid follicular, thyroid papillary, or uterine. In another aspect, the method further comprises the step of detecting and determining a tissue of origin of a human cancer at least 1, 2, 3, 4, 5, 6, 7, 8, 9, 10, or 20 years in advance of clinical symptoms. In another aspect, the method further comprises the step of performing an enzyme linked immunoassay with an antibody to SEQ ID NO. 2 in a point of care test to detect ENOX2 presence in blood sera or other body fluids. In one aspect, silver is replaced with gold.

In another embodiment, the present invention includes a semi-quantitative method for the detection of ENOX2 transcript variants from one or more anti-ENOX2 antibody-binding spots comprising the steps of: obtaining a substrate onto which proteins obtained from concentrated blood, serum, or plasma sample from a subject have been transferred electrophoretically; separating the one or more ENOX2 transcript variants from the one or more anti-ENOX2 antibody-binding spots; and measuring an ENOX2-catalyzed conversion of an ionic gold or ionic silver to colloidal gold or colloidal silver, respectively, by light scattering from the one or more anti-ENOX2 antibody binding spots on the substrate, wherein each of the one or more spots is indicative of an ENOX2 transcript variant.

In another embodiment, the present invention includes a semi-quantitative method for the detection of ENOX2 transcript variants from one or more anti-ENOX2 antibody-binding spots comprising the steps of: obtaining a substrate onto which proteins obtained from concentrated blood, serum, or plasma sample from a subject have been transferred electrophoretically; separating the one or more ENOX2 transcript variants from the one or more anti-ENOX2 antibody-binding spots; and measuring the ENOX2-catalyzed conversion of ionic silver to colloidal silver is defined further as comprising the steps of: obtaining a core from the one or more anti-ENOX2 antibody-binding spots suspected of comprising at least one ENOX2 transcript variant separated by molecular weight and isoelectric point; incubating the core with silver oxide in solution to form colloidal silver; developing the colloidal silver; and measuring the amount and/or presence of colloidal silver at 350-650 nm by comparing the light from the core with light from a background core that did not contain an ENOX2 transcript variant.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

All malignant cells and tissues express one or more members of a unique family of cell surface ubiquinone (NADH) oxidases with protein disulfide interchange activity (ENOX2 proteins) that are specific to cancer, absent from non-cancer cells and tissues and are shed into the blood. Multiple ENOX2 transcript variants share a common cancer-specific antibody recognition sequence that allows for detection using a common recombinant ENOX2 specific antibody (scFv). Cancer of different cellular or tissues of origin express different ENOX2 transcript variants or combinations of transcript variants that allow for the identification of the cell type and/or tissue of origin based on the patterns of molecular weight and isoelectric points of the transcript variants present in serum or plasma. All 36 transcript variants represented in the data base yielded values ≥7% above background (average 12%) consistent with a structure containing the common Exon 5 that defines ENOX2 and includes the ENOX2 specific antibody and drug-combining site E145EMTE. Also provided is the basis for a point of care test to detect ENOX2 transcript variants based on use of colloidal silver or gold complexes with ENOX2 as a rapid simple test for cancer presence.

ENOX2 transcript variants are identified on the basis of their molecular weights and isoelectric point with detection using a ENOX2-specific monoclonal antibody (MAb) (U.S. Pat. No. 7,053,188), using single chain variable region (scFv) fragment which recognizes all cell surface NOX proteins (both age-related, normal cell and neoplasia specific NADH oxidase) or using polyclonal sera raised against ENOX2. The ECTO-NOX proteins are first enriched and concentrated from a biological sample, desirably a serum sample, by binding to nickel-agarose and then eluting. After release of the proteins from the nickel agarose by vortexing, the proteins are separated in the first dimension by isoelectric focusing and in the second dimension by polyacrylamide gel electrophoresis. In one example, the isoelectric focusing step is over a pH range from 3 to 10, and size separation is over a 10% polyacrylamide gel. Most of the cancer-specific ENOX2 isoforms exhibit isoelectric points in a very narrow range between pH 3.9 and 6.3 but differ in molecular weight from 34 to 136 kDa. In a 2D gel system, the cancer-specific isoforms are located in Quadrants I (relatively high molecular weight material) and IV (lower molecular weight material, notably the range of 30 to 30 kDa. IgG heavy chains (Quadrant II and IgG light chains (Quadrant III) cross react with the scFv antibody and along with reference proteins at 53 and 79 to 85 kDa serve as loading controls. The absence of all ENOX2 isoforms indicates the absence of cancer. The presence of an ENOX2 isoform indicates the presence of cancer. The particular molecular weight present in a serum sample or a particular combination of isoforms provides an indication of the cell type or tissue of origin of the cancer. The method not only determines cancer presence, but also the method of the present invention provides diagnostic information concerning the tissue of origin. At present there are no other pan cancer (all forms of human cancer) tests with these particular capabilities. ENOX2 proteins with apparent molecular weights of about 64, 66 and/or 68 kDa. pH 4.5 are associated with breast cancer. ENOX2 protein of 52 kDa, pH 4.3 is associated with small cell lung cancer.

Where a patient is suspected of having cancer, a biological sample, advantageously a serum sample can be prepared, and the 2D gel electrophoresis/immunological analysis of the present invention can be undertaken to provide for spots on the paper, film or substrate onto which the proteins have been blotted for later isolation, e.g., using a coring tool.

Figure 1A:
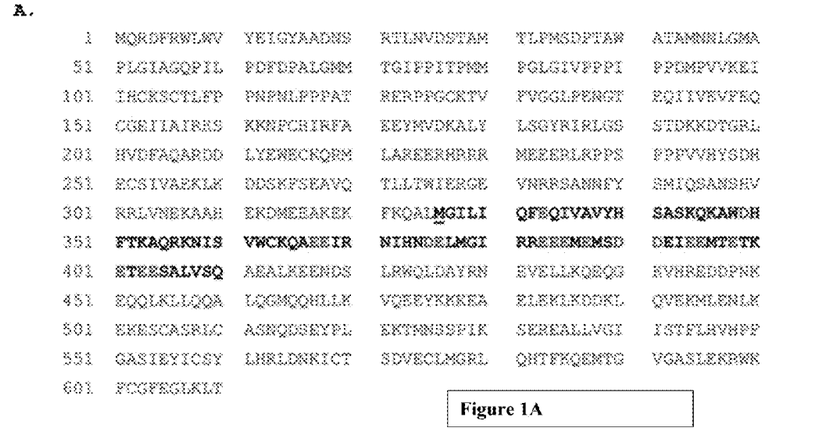
FIG. 1A shows the amino acid sequence of the full length recombinant ENOX2 protein (SEQ ID NO:1). The inter coil region of Exon 5 is highlighted in bold.
Figure 1B:
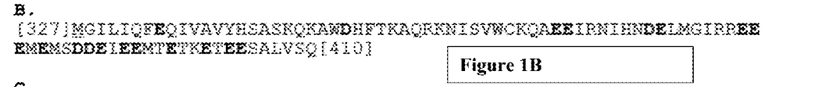
FIG. 1B shows the amino acid sequence of the Exon 5 inter coil region. Acidic amino acids are highlighted in bold. The Exon5 inter coil region starts at reside 327 and terminates at residue 410, is 85 amino acids long, and has an estimated molecular weight of 10 kDa (SEQ ID NO:2).
Figure 1C:
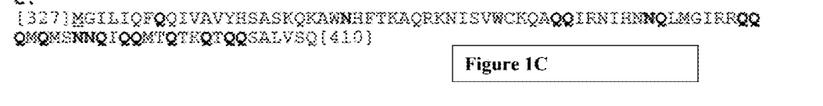
FIG. 1C shows the amino acid sequence of the EXON 5 inter coil region with acidic amino acids mutated to their amide form highlighted in bold. The mutant peptide is also 85 amino acids long and has an estimated molecular weight of 10 kDa. (SEQ ID NO:3).

The approach is based on an early discovery that tetrasilver tetroxide (TST) a potential anti-cancer agent based on clinical trials (U.S. Patent No. 2004/0205827), was targeted specifically to ENOX2 (Morré et. al., 2004. *Molecular Biol Cell* 15 (Suppl): 250a). The TST complex of two monovalent silver (AgI) and two trivalent silver (AgIII) ions bound with four oxygen atoms ($O^{-2}$) combines covalently with ENOX2. Comparing human cervical carcinoma (HeLa) cells and MCF-10A cells, the HeLa cells bound TST to their cell surface whereas the non-cancer MCF-10A cells did not (Morré et. al., 2004. *Molecular Biol Cell* 15 (Suppl): 250a). More important, TST immobilized onto magnetic beads specifically bound ENOX2 released from HeLa surfaces, cancer sera and recombinant bacterially expressed ENOX2 proteins. A colorimetric method to assess the TST-ENOX2 protein complex based on enhanced silver binding and dissection of recombinant ENOX2 proteins into specific domains expressed in bacteria revealed that the peptide contributed by ENOX2 Exon 5 containing the cancer-specific ENOX2 antibody combining sequence E145EMTE was also the portion of the ENOX2 protein responsible for TST-binding (FIGS. 1A, 1B and 1C).

SEQ ID NOS. 1, 2 and 3, respectively:

```
A.
  1 MQRDFRWLWV YEIGYAADNS RTLNVDSTAM TLPMSDPTAW ATAMNNLGMA

51 PLGIAGQPIL PDFDPALGMM TGIPPITPMM PGLGIVPPPI PPDMPVVKEI

101 IHCKSCTLFP PNPNLPPPAT RERPPGCKTV FVGGLPENGT EQIIVEVFEQ

151 CGEIIAIRKS KKNFCHIRFA EEYMVDKALY LSGYRIRLGS STDKKDTGRL

201 HVDFAQARDD LYEWECKQRM LAREERHRRR MEEERLRPPS PPPVVHYSDH

251 ECSIVAEKLK DDSKFSEAVQ TLLTWIERGE VNRRSANNFY SMIQSANSHV

301 RRLVNEKAAH EKDMEEAKEK FKQALMGILI QFEQIVAVYH SASKQKAWDH

351 FTKAQRKNIS VWCKQAEEIR NIHNDELMGI RREEEMEMSD DEIEEMTETK

401 ETEESALVSQ AEALKEENDS LRWQLDAYRN EVELLKQEQG KVHREDDPNK

451 EQQLKLLQQA LQGMQQHLLK VQEEYKKKEA ELEKLKDDKL QVEKMLENLK

501 EKESCASRLC ASNQDSEYPL EKTMNSSPIK SEREALLVGI ISTFLHVHPF

551 GASIEYICSY LHRLDNKICT SDVECLMGRL QHTFKQEMTG VGASLEKRWK

601 FCGFEGLKLT

B.
[327]MGILIQFEQIVAVYHSASKQKAWDHFTKAQRKNISVWCKQAEEIRNIHNDELMGIRREE
EMEMSDDEIEEMTETKETEESALVSQ[410]

C.
[327]MGILIQFQQIVAVYHSASKQKAWNHFTKAQRKNISVWCKQAQQIRNIHNNQLMGIRRQQ
QMQMSNNQIQQMTQTKQTQQSALVSQ[410]
```

ENOX2 proteins of 52 and 80 kDa, pH 4.1 and 4.2 characterize ovarian cancer. ENOX2 isoforms of about 75 kDa, pH 6.3 are associated with prostate cancer. An ENOX2 protein of about 94 kDa, pH 5.4 is associated with cervical cancer. ENOX2 proteins of about 34 and 52 kDa, pH 4.3 and 3.9 are characteristic of colon cancer. An ENOX2 isoform of 54 kDa, pH 5.1 is associated with non-small cell lung cancer.

The TST-binding portion of an ENOX2 Exon 5 contains a sequence of 85 amino acids of which 19 are acidic amino acids (glutamic acid and aspartic acid) and of which 10 occur as acidic pairs or triads. When the acidic amino acids are replaced with their corresponding amides, the peptides no longer bind silver. A similar phenomenon is encountered where polymeric gamma carboxy glutamic acid is employed to bind silver to form nanoparticles used in cancer drug delivery (Manocha and Marguritis, 2008. *Crit Rev Biotechnol* 37: 795-808).

Figure 2:
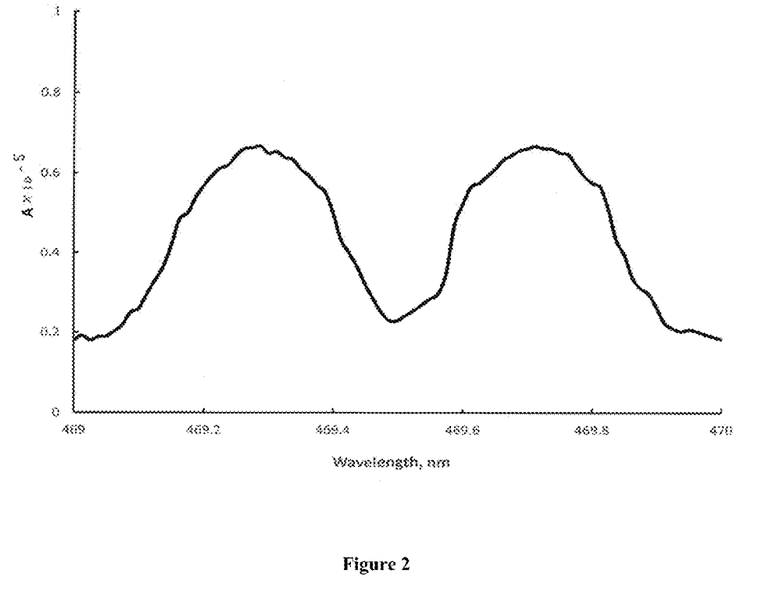
FIG. 2 is a graph that shows the absorbance spectra of ENOX2 transcript variant from sera of a breast cancer patient showing the double maxima corresponding to the two symmetry axes of the silver nanoparticles centered at 469.3 and 469.7 nm.

In order to visualize silver nanoparticle formation by ENOX2 proteins, the bound tetrasilver tetroxide was reduced using the antioxidant polyphenol epigallocatechin gallate (EGCg), a specific inhibitor of ENOX2 activity that combines with the E145EMTE drug-binding site of ENOX2. A commercially available (Ted Pella, Redding, Calif.) silver enhancement reagent is then added to increase the size of the nanoparticle and a biphasic red shift in absorbance is seen centered at 469.3 and 469.7 nm measured spectrophotometrically (FIG. 2).

Regions of western blots occupied by ENOX2 antibody-reactive proteins were excised by coring, reacted with tetrasilver tetroxide containing EGCg followed by silver enhancement with formation of reduced silver nanoparticles, analyzed spectrophotometrically and compared to a background core from the same western blot. Results are recorded as area under the absorbance curve compared to cores from proteins from blot regions not corresponding to proteins in the database (Table 2).

Both nanoparticle diameter and geometry influence the location and number of UV-visible bands. With nanorods, such as these, the double peaks occur as a result of oscillations along each of the two principle axes of symmetry, one along the transverse axis and one along the longitudinal axis (Jiang, et al. 2014. Scientific Reports 4:5323-5330).

Figure 3:
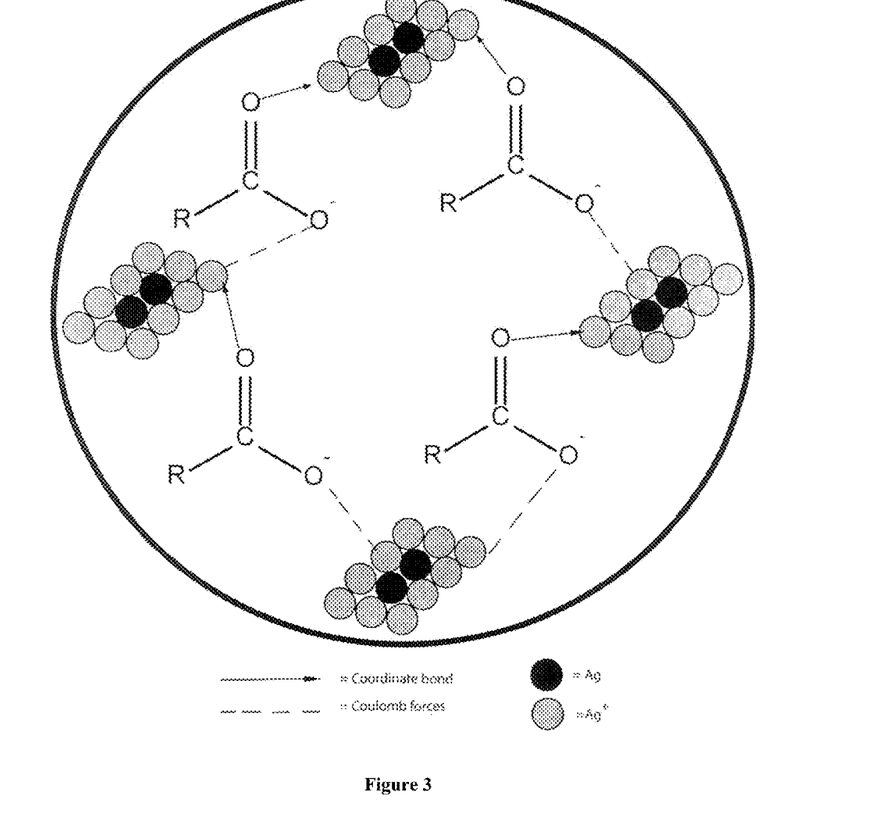
FIG. 3 is a diagrammatic representation of the proposed organization of silver nanoparticles bound to acidic amino residues of the ENOX2 exon 5 derived peptide containing the E145EMTE sequence common to all ENOX2 transcript variants.
Figure 4:
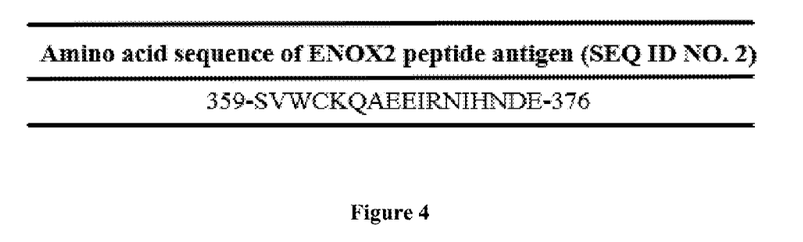
FIG. 4 is the amino acid sequence of ENOX2 peptide antigen (SEQ ID NO. 4).

According to the location of the absorbance maxima (Jiang, et al. 2014. Scientific Reports 4:5323-5330), the ENOX2-generated nanoparticles are ellipsoids 75-85 nm in diameter and are organized in tetrads bound by both coordinate bonds and coulombic forces as diagrammed in FIG. 3, bound to regularly spaced acidic amino acid residues within the Exon 5-derived protein structure common to all ENOX2 transcript variants. These particles are absent (0.7±2.8% above background) based on measurements from 2,525 western blot cores taken from regions not occupied by proteins corresponding to ENOX2 transcript variants (Table 2).

TABLE 1

Ranges for Molecular Weight (MW) and Isoelectric Point (Pi) Determined for Sera of Patients Diagnosed with 24 Different Cancers Representing 20 Different Tissues of Origin

| | | RANGES | | | | | |
|---|---|---|---|---|---|---|---|
| | | Protein 1 | | Protein 2 | | Protein 3 | |
| Cancers | N | MW (kDa) | Pi (pH) | MW (kDa) | Pi (pH) | MW (kDa) | Pi (pH) |
| Bladder | 37 | 63-66 | 4.2-5.6[1] | 42-48 | 4.1-4.8[1] | | |
| *Blood Cell (Total) | (117) | 34-47 | 3.5-4.6 | | | | |
| Breast | 682 | 64-69 | 4.2-4.9 | | | | |
| Cervical | 47 | 90-100 | 4.2-5.4 | | | | |
| Colorectal | 125 | 80-96 | 4.4-5.4 | 50-65 | 4.2-5.3 | 33-46 | 3.8-5.2 |
| Esophageal | 26 | 42-47 | 4.6-5.2 | | | | |
| Gastric | 26 | 120-188 | 4.7-5.5 | 50-62 | 4.5-5.6 | 45-53 | 2.4-3.6 |
| Hepatocellular | 31 | 58-70 | 4.5-5.0 | 34-40 | 4.1-5.2 | | |
| Leukemias | 36 | 34-45 | 3.5-4.5 | | | | |
| **Lung, Non-Small Cell | 55 | 53 | 4.7-5.3 | | | | |
| **Lung, Non-Small Cell | 270 | 54-56 | 4.6-5.3 | | | | |
| Lung, Small Cell | 27 | 52-53 | 4.1-4.6 | | | | |
| Lymphomas | 56 | 43-45 | 3.5-4.5 | | | | |
| Melanoma | 51 | 37-41 | 4.6-5.3 | | | | |
| Mesothelioma | 27 | 60-68 | 3.8-4.1 | 38-44 | 3.8-4.6 | | |
| Myelomas | 25 | 40-45 | 3.9-4.6 | | | | |
| Ovarian | 115 | 72-90 | 3.7-5.0 | 37-47 | 3.7-5.0 | | |
| Pancreatic | 75 | 48-51 | 3.9-5.4 | | | | |
| Prostate | 361 | 71-88 | 5.1-6.5 | | | | |
| Renal Cell (Kidney) | 31 | 69-73 | 4.7-5.4 | 54-61 | 4.1-5.2 | 38-43 | 3.7-4.3 |
| Sarcoma | 29 | 50-55 | 5.2-5.6 | 37-45 | 4.3-4.9 | | |
| Squamous Cell | 51 | 57-68 | 5.0-5.4 | | | | |
| Testicular Germ Cell | 25 | 61-62 | 5.0-5.4 | 40-45 | 4.4-4.7 | | |
| Thyroid Follicular | 25 | 48-56 | 4.7-5.1 | 37-42 | 4.5-5.2 | | |
| Thyroid Papillary | 27 | 56-67 | 4.5-5.0 | 37-44 | 3.2-3.6 | | |
| ***Uterine (Endometrial) | 26 | 63-66 | 4.2-4.9[2] | 41-48 | 4.4-5.6[2] | | |
| ***Uterine (Endometrial) | 57 | 67-71 | 4.2-5.1 | 41-48 | 3.7-5.4 | | |
| Total | 2460 | | | | | | |

*Blood cell cancers include lymphomas, leukemias and myelomas already represented in the totals.

**Non-Small Cell Lung cancers are in two subsets to avoid molecular weight overlap with small cell lung cancer.

***Uterine cancers are in two subsets based on molecular weight to avoid overlap with bladder cancer (see footnotes 1 and 2).

[1]Isoelectric point pH of Protein 1 ≥ Protein 2.

[2]Isoelectric point pH of Protein 1 < Protein 2.

TABLE 2

Validation of all 36 ONCOblot Transcript Variants Representing 20 Cancer Tissues of Origin as Being Transcript Variants of ENOX2.

| | | Absorbance, % Above Background | | | | | |
|---|---|---|---|---|---|---|---|
| | | Protein 1 | | Protein 2 | | Protein 3 | |
| Cancer Tissue of Origin | N | Mean ± SD | Range | Mean ± SD | Range | Mean ± SD | Range |
| Bladder | 26 | 12.6 ± 3.6 | 8-21 | 14.2 ± 7.2 | 7-31 | | |
| Blood Cell* | 52 | 12.6 ± 4.4 | 8-28 | | | | |
| Breast | 525 | 12.3 ± 3.7 | 7-31 | | | | |
| Cervical | 36 | 11.8 ± 4.7 | 7-25 | | | | |
| Colorectal | 116 | 12.5 ± 3.4 | 8-25 | 11.9 ± 4.2 | 7-29 | 10.9 ± 3.7 | 7-21 |
| Esophageal | 9 | 10.7 ± 4.0 | 9-15 | | | | |
| Gastric | 21 | 13.8 ± 3.5 | 9-18 | 12.2 ± 3.2 | 8-18 | 11.1 ± 3.4 | 8-15 |
| Hepatocellular | 18 | 13.1 ± 3.6 | 7-19 | 10.9 ± 4.3 | 8-17 | | |
| Lung | 92 | 12.5 ± 4.2 | 7-26 | | | | |
| Melanoma | 22 | 12.8 ± 3.5 | 8-22 | | | | |
| Mesothelioma | 11 | 15.6 ± 3.3 | 11-20 | 15.9 ± 5.7 | 10-25 | | |
| Ovarian | 20 | 13.2 ± 4.5 | 8-26 | 12.0 ± 4.0 | 8-21 | | |
| Pancreatic | 23 | 12.4 ± 4.4 | 8-24 | | | | |
| Prostate | 165 | 12.2 ± 3.9 | 8-32 | | | | |
| Renal Cell (Kidney) | 19 | 11.6 ± 3.1 | 8-16 | 10.5 ± 2.9 | 7-17 | 9.6 ± 1.7 | 8-14 |
| Sarcoma | 13 | 12.2 ± 3.9 | 9-18 | 12.3 ± 4.1 | 9-19 | | |
| Squamous Cell | 35 | 12.5 ± 3.5 | 8-24 | | | | |
| Testicular Germ Cell | 15 | 10.0 ± 3.7 | 8-16 | 10.3 ± 3.0 | 8-17 | | |
| Thyroid Follicular** | 12 | 11.2 ± 3.7 | 7-17 | 11.2 ± 2.5 | 8-17 | | |
| Thyroid Papillary** | 21 | 11.2 ± 2.7 | 9-19 | 13.2 ± 5.6 | 8-21 | | |
| Uterine (Endometrial) | 96 | 10.9 ± 2.9 | 8-19 | 10.7 ± 4.2 | 7-20 | | |
| Total Cancer | 1496 | | | | | | |
| Non-Cancer | 2525 | 0.7 ± 2.8 | −3.5-6 | | | | |

*Blood cell cancers include lymphomas, leukemias, and myelomas
**Two different cancers from a single tissue of origin (thyroid)

For all transcripts variants with molecular weights and isoelectric points corresponding to those listed in the ONCOblot® Tissue of Origin Test Table of Ranges (Table 1), absorbance values ranged from 7 to 30% above background with a mean value of 12% (Table 2).

Out of range proteins do not form nanoparticles based 2,525 out of range protein samples. The values averaged 0.7±2.8% above background and did not generate absorbance spectra with maxima at 469.3 and 469.7 nm characteristic of ENOX2 proteins. Values of ≤0.5±2 standard deviations from the mean (6% above background) were considered to be statistically unrelated (99% confidence interval) to ENOX2 or to ENOX2 proteins at levels below the practical limit of detection. The unreactive proteins included serum albumin and immunoglobulin as well as the immune reactive reference proteins pH 4.1 and pH 6.8.

For a Point-of-Care Strip Test the basic principle is that of a gold or silver nanoparticle-based pregnancy test. To maximize test specificity, ENOX2 peptide immunogen comprised from about 8 to about 15 contiguous amino acids derived from a region of ENOX2 adjacent to the quinone binding site will be utilized. In a preferred embodiment, the ENOX2 peptide antigen is 359-SVWCKQAEEIRNIHNDE-376 (SEQ ID NO. 4) (Table 4).

EXAMPLES

The disclosure is further described by the following illustrative examples. The examples do not limit the disclosure in any way.

Example 1

Western blots occupied by ENOX2 antibody reactive proteins, as well a background region, were excised by coring. The background region was selected at a pH closely matching the antibody reactive region, but not overlapping any detected protein. Cored samples were stored in 0.5 mL Eppendorf tubes for up to 1 week before further processing.

A silver (III) oxide (AgO)/epigallocatechin-3gallate (EGCg) solution was prepared as follows: 6 mg AgO (Sigma-Aldrich, St. Louis, Mo.) was added to a 970 μL aliquot of $H_2O$ and 30 μL of a 10 mM epigallocatechin-3-gallate (EGCg) (Sigma-Aldrich, St. Louis, Mo.) solution was added to 970 μL of EtOH to prepare an intermediate 0.3 mM solution. A portion (30 μL) of the 0.3 mM EGCg solution was added to the AgO solution and vortexed, yielding a saturated solution. The AgO/EGCg solution was then centrifuged for 60 sec at maximum speed to remove excess AgO. The resulting mixture has a slight yellow color. A fraction (90 μL) of the centrifuged AgO/EGCg solution was added to each Eppendorf tube containing a cored sample, and samples were incubated in total darkness for 2-4 hr.

A 'developer' solution was mixed at the end of the incubation period and used immediately. The developer solution was created by mixing equal parts of an initiator and enhancer solution (Ted Pella, Redding, Calif.) and vortexing.

Cored samples reacted with AgO containing EGCg, followed by silver enhancement, resulted formation of reduced silver nanoparticles as determined by spectrophotometrically (Olis, D W 2000 Conversion). Both nanoparticle diameter and geometry influence the location and number of UV-visible bands. With nanorods multiple peaks occur as a result of electronic oscillations along each of the two principle axes of symmetry, one along the longitudinal axis and one along the transverse axis (Jiang, et al. 2014. *Scientific Reports* 4:5323-5330). The antibody reactive cores were compared to a background core from the same western blot.

Results are recorded as area under the absorbance curve, comparing the area of anti-body reactive spots to the paired background spot.

In order to visualize silver nanoparticle formation by ENOX2 proteins, the bound tetra silver tetroxide was reduced using the antioxidant polyphenol epigallocatechin gallate (EGCg), a silver enhancement reagent, is then added to increase the size of the nanoparticle and a red shift in absorbance is seen with bimodal maxima centered at 469.3 and 469.7 nm measured spectrophotometrically (FIG. 2).

Example 2

TST immobilized onto magnetic beads specifically binds ENOX2 released from HeLa surfaces, cancer sera and recombinant bacterially expressed ENOX2 proteins. A colorimetric method to assess the TST-ENOX2 protein complex based on enhanced silver binding and dissection of recombinant ENOX2 proteins into domains expressed in bacteria revealed that the peptide contributed by ENOX2 Exon 5 containing the cancer-specific ENOX2 antibody combining sequence E145EMTE was also the portion of the ENOX2 protein responsible for TST-binding (FIG. 1A).

Example 3

The TST-binding portion of an ENOX2 Exon 5 contains a sequence of 85 amino acids of which 19 are acidic amino acids (glutamic and aspartic) and of which 13 occur as acidic pairs or triads. When the acidic amino acids are replaced with their corresponding amides by site-directed malignancies, the peptides no longer bound silver. A similar situation is encountered where polymeric gamma carboxy glutamic acid is employed to bind silver to form nanoparticles used in cancer drug delivery.

Example 4

Electrons in the conduction band of silver nanoparticles exhibit coherent vibrational oscillations when excited by an electric field. The oscillations are driven by a combination of the externally applied electric field and the restorative Coulombic attraction between electrons and atomic nuclei. Four factors determine the frequency of oscillations: the density of electrons, the effective electron mass, and the shape and size of the charge distribution. The 'dipole plasma resonance' of the particle is the term used to refer to the collective oscillation of the conduction electrons (Kelly, et al. 2003. *Journal of Physical Chemistry* 107: 668-677).

Example 5

It has been experimentally demonstrated that both particle diameter and geometry influence the location and number of UV-visible absorbance maxima. The amount of red-shift in absorbance maxima correlates with the particle size (Agnihotri et. al., 2014. *RSC Advances* 4(8): 3974-3983; Mock et. al., 2002. *American Institute of Physics* 116: 6755). Additionally, the location of the absorbance peak is influenced by the particle geometry (Mock et. al., 2002. *American Institute of Physics* 116: 6755). In the case of asymmetrical particles, such as nanorods, multiple absorbance peaks occur owing to oscillations along each of the principle axes of symmetry. For a nanorod, two absorbance peaks occur, one along the longitudinal axis and one along the transverse axis (Jiang, et al. 2014. *Scientific Reports* 4: 5323-5330).

Example 6

Two closely spaced absorbance maxima in the UV-visible spectra of solubilized serum proteins from cancer patients processed using the observed protocol (FIG. 2). Proteins were separated by means of two-dimensional gel electrophoresis and stained with an antibody specific to the cancer-specific protein ENOX2. Protein bands of corresponding size and isoelectric focusing points were extricated from the nitrocellulose gel and dissolved in aqueous solution. The solution is treated with BPI silver enhancer as well as EGCg. Serum proteins from cancer patients display two absorbance maxima at 469.3 and 469.7 nm (FIG. 2). The absorbance maxima that are attributed to the formation of silver nanoparticles.

Example 7

ENOX2 binds soluble silver (II) ions that are added to the serum sample as silver (II) oxide (Ago) in the spot-check protocol. Silver (II) ions are reduced by EGCg. The reduction potential for silver (II) is 0.80 V while the oxidation potential for EGCg is −0.020 V (Yang et. al., 2001. *Chemical and Pharmaceutical Bulletin* 49: 747-751). The sum of the redox potentials is positive, implying that the reaction occurs spontaneously. Insoluble silver metal forms as a product of the redox reaction, and aggregates into ellipsoid particles with slightly different longitudinal and transverse lengths (FIG. 3). According to the location of the absorbance maxima the particles are roughly 15.5-116.0 nm in diameter. Findings show that the presence of these particles is either greatly reduced or absent from protein bands that do not contain ENOX2.

Example 8

The presence of silver nanoparticles, detectable by the technique described above, is indicative of the presence of ENOX2 and is therefore a means to confirm the presence of cancerous pathology from the blood serum of suspected cancer patients. ENOX2 is shed into serum and is detectable by ENOX2-specific antibodies as well as characteristic molecular weights and isoelectric focusing points. The presence of ENOX2 is now further confirmed by the presence of silver nanoparticles after treatment with silver enhancer and EGCg, offering an alternative assessment of the cancerous origin of proteins indicated by two-dimensional gel electrophoresis.

Example 9

A point-of-care, test based on silver nanoparticle formation utilized the peptide antibody (SEQ ID NO. 2) (FIG. 4) and the principle of a pregnancy test.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed:

1. A semi-quantitative method for the detection of ENOX2 isoform variants from one or more anti-ENOX2 antibody-binding spots comprising the steps of:
   electrophoretically separating proteins from a concentrated blood, serum, or plasma sample from a subject;
   transferring the electrophoretically separated proteins to a substrate;
   separating and removing the one or more ENOX2 isoform variants from the one or more anti-ENOX2 antibody-binding spots on said substrate; and
   measuring an ENOX2-catalyzed conversion of an ionic gold or ionic silver to colloidal gold or colloidal silver, respectively, detected by light scattering from the one or more anti-ENOX2 antibody binding spots on the substrate, wherein each of the one or more spots is indicative of an ENOX2 isoform variant.

2. The method of claim 1, wherein quantitation is achieved by removing ENOX2 antibody reactive spots from the blot with a cork borer and quantitating the amount of ENOX2 using elution and reaction with ionic silver or gold to form silver nanoparticles and their quantitation measured by light scattering when compared to a background sample.

3. The method of claim 1, wherein a signal above a background confirms the present of the ENOX2 isoform.

4. The method of claim 1, further comprising the step of measuring the ENOX2-catalyzed conversion of ionic silver to colloidal silver is defined further as comprising the steps of:
   obtaining a core from the one or more anti-ENOX2 antibody-binding spots suspected of comprising at least one ENOX2 isoform variant separated by molecular weight and isoelectric point;
   incubating the core with silver or gold oxide in solution to form colloidal silver or gold; and
   developing the colloidal silver; and
   measuring the amount and/or presence of colloidal silver at 350-650 nm by comparing the light from the core with light from a background core that did not contain an ENOX2 isoform variant.

5. The method of claim 4, wherein the light scattering is a doublet at 469.3 and 469.7 nm.

6. The method of claim 1, wherein the tissue of origin of the cancer detected is selected from at least one of bladder, blood cell, lymphomas, leukemias, multiple myelomas and myelomas, breast, cervical, colorectal, esophageal, gastric, hepatocellular, small cell lung, non-small cell lung, melanoma, mesothelioma, ovarian, pancreatic, prostate, renal cell (kidney), sarcoma, squamous cell, testicular germ cell, thyroid follicular, thyroid papillary, or uterine.

7. The method of claim 1, further comprising the step of detecting and determining a tissue of origin of a human cancer at least 1, 2, 3, 4, 5, 6, 7, 8, 9, 10, or 20 years in advance of clinical symptoms.

8. The method of claim 1, where by the principle of a colloidal gold or silver-based pregnancy test using an antibody to SEQ ID NO. 2 is used as a point of care test to detect ENOX2 presence in blood sera or other body fluids.

9. The method of claim 1, further comprising measuring colloidal gold.

10. A semi-quantitative method for the detection of ENOX2 isoform variants from one or more anti-ENOX2 antibody-binding spots comprising the steps of:
    obtaining a substrate onto which proteins obtained from concentrated blood, serum, or plasma sample from a subject have been transferred electrophoretically;
    separating and removing the one or more ENOX2 isoform variants from the one or more anti-ENOX2 antibody-binding spots on said substrate; and
    measuring an ENOX2-catalyzed conversion of an ionic gold or ionic silver to colloidal gold or colloidal silver, respectively, by light scattering from the one or more anti-ENOX2 antibody binding spots on the substrate, wherein each of the one or more spots is indicative of an ENOX2 isoform.

11. The method of claim 10, wherein quantitation is achieved by removing ENOX2 antibody reactive spots from the blot with a cork borer and quantitating the amount of ENOX2 using elution and reaction with ionic silver or gold to form silver nanoparticles and their quantitation measured by light scattering when compared to a background sample.

12. The method of claim 10, wherein a signal above a background confirms the present of the ENOX2 isoform variant.

13. The method of claim 10, further comprising the step of measuring the ENOX2-catalyzed conversion of ionic silver to colloidal silver is defined further as comprising the steps of:
    obtaining a core from the one or more anti-ENOX2 antibody-binding spots suspected of comprising at least one ENOX2 isoform variant separated by molecular weight and isoelectric point;
    incubating the core with silver or gold oxide in solution to form colloidal silver or gold; and
    developing the colloidal silver; and
    measuring the amount and/or presence of colloidal silver at 350-650 nm by comparing the light from the core with light from a background core that did not contain an ENOX2 isoform variant.

14. The method of claim 13, wherein the light scattering is a doublet at 469.3 and 469.7 nm.

15. The method of claim 10, wherein the tissue of origin of the cancer detected is selected from at least one of bladder, blood cell, lymphomas, leukemias, multiple myelomas and myelomas, breast, cervical, colorectal, esophageal, gastric, hepatocellular, small cell lung, non-small cell lung, melanoma, mesothelioma, ovarian, pancreatic, prostate, renal cell (kidney), sarcoma, squamous cell, testicular germ cell, thyroid follicular, thyroid papillary, or uterine.

16. The method of claim 10, further comprising the step of detecting and determining a tissue of origin of a human cancer at least 1, 2, 3, 4, 5, 6, 7, 8, 9, 10, or 20 years in advance of clinical symptoms.

17. The method of claim 10, where by the principle of a colloidal gold or silver-based pregnancy test using an antibody to SEQ ID NO. 2 is used as a point of care test to detect ENOX2 presence in blood sera or other body fluids.

18. The method of claim 10, further comprising measuring colloidal gold.

19. The method of claim 10, wherein the substrate is elected from nitrocellulose, nylon, or polyvinylidene difluoride.

20. A semi-quantitative method for the detection of ENOX2 isoform variants from one or more anti-ENOX2 antibody-binding spots comprising the steps of:
obtaining a substrate onto which proteins obtained from concentrated blood, serum, or plasma sample from a subject have been transferred electrophoretically;
separating and removing the one or more ENOX2 isoform variants from the one or more anti-ENOX2 antibody-binding spots on said substrate;
measuring the ENOX2-catalyzed conversion of ionic silver to colloidal silver is defined further as comprising the steps of:
obtaining a core from the one or more anti-ENOX2 antibody-binding spots suspected of comprising at least one ENOX2 isoform variant separated by molecular weight and isoelectric point;
incubating the core with silver oxide in solution to form colloidal silver;
developing the colloidal silver; and
measuring the amount and/or presence of colloidal silver at 350-650 nm by comparing the light from the core with light from a background core that did not contain an ENOX2 isoform variant.

* * * * *